US008728052B2

(12) United States Patent
Wang et al.

(10) Patent No.: US 8,728,052 B2
(45) Date of Patent: May 20, 2014

(54) CONVERTIBLE REUSABLE DIAPER

(76) Inventors: Jinmei Wang, Markham (CA); Yu Ping, Dublin, CA (US)

( * ) Notice: Subject to any disclaimer, the term of this patent is extended or adjusted under 35 U.S.C. 154(b) by 41 days.

(21) Appl. No.: 13/417,009

(22) Filed: Mar. 9, 2012

(65) Prior Publication Data
US 2013/0237940 A1 Sep. 12, 2013

(51) Int. Cl.
*A61F 13/15* (2006.01)
(52) U.S. Cl.
USPC ............................ 604/399; 604/398; 604/397
(58) Field of Classification Search
USPC .......................................... 604/395, 397–402
See application file for complete search history.

(56) References Cited

U.S. PATENT DOCUMENTS

| 5,707,364 | A * | 1/1998 | Coates | 604/391 |
| 6,579,273 | B2 * | 6/2003 | Dupuy | 604/385.14 |
| 2010/0036353 | A1 * | 2/2010 | Payne | 604/385.08 |
| 2012/0010585 | A1 * | 1/2012 | Labit et al. | 604/372 |

* cited by examiner

*Primary Examiner* — Melanie Hand
*Assistant Examiner* — Aundria Hairell (57) ABSTRACT

A convertible reusable diaper is provided, comprised of an outer cover portion, a liner portion, and a detachable absorption portion. The outer cover portion may generally include barrier panels attached at both the front and rear regions of the outer cover portion to form interior pockets. A plurality of fastenable tabs attached to hole-openings at the barrier panels affixes the liner portion or the detachable absorption portion in place. The hole-openings allow the passage of the fastenable tabs through the barrier panels. Both the liner portion and the detachable absorption portion include fastener members inter-engaged with the corresponding fastener members located at the fastenable tabs to allow the liner portion or the detachable absorption portion to be removably affixed to the outer cover portion. Numerous options for affixing the insert portion and the detachable absorption portion allow conversion to different diaper designs.

20 Claims, 10 Drawing Sheets

CONVERTIBLE REUSABLE DIAPER

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

BACKGROUND OF THE INVENTION

The increased ecological awareness has led to a growth in campaign for parents to turn away from disposable diaper products and choose reusable alternatives instead, such as cloth or hybrid diapers. Cloth diapers traditionally consisted of a folded square or rectangle of cloth, fastened with safety pins and required constant monitoring and changing because they quickly became soggy or soiled with feces. They must be washed after each diaper change. Although the usage of "stay-dry" wicking liner and waterproof exteriors or water-resistant outer shell in modern cloth diapers alleviates some of the need for constant changing and washing everything after each diaper change, how to make a diaper that can be adjusted, easily assembled, cleaned to accommodate different absorption and containment requirements of body discharged as well as size requirements to correspond with baby's growing weight still remains to be a challenge.

There are different types and brands of cloth diapers available on the market, including impermeable diaper covers, pocket diapers, all-in-one and all-in-two diapers with waterproof exteriors, etc. Different diapers work better for different situations and none seems to be perfect on their own. For example, at home, a pocket diaper or a diaper cover with reusable insert pads works best. However, they generally are bulky and don't work really well under most clothes, making parents reluctant to use when going out. Although all-in-one and all-in-two diapers are a bit trimmer while still providing good absorbency, they are more expensive and dry time is much longer than regular cloth diapers that go with a cover and pocket diapers, taking up more drying cycles.

Therefore, it would be desirable to provide a convertible reusable diaper product which combines the best of all the aforementioned diaper designs in the prior art and can be conveniently assembled and adjusted to correspond with different occasions by converting among different designs, for instance, by simply re-affixing the detachable absorption portion and the liner portion and changing the insert types, the product can be converted from a pocket diaper into an all-in-two diaper. It is also desired for this convertible reusable diaper to have short dry time and allow the usage of most reusable insert products produced by a wide range of vendors made as well as allowing the usage of biodegradable eco-friendly disposable inserts.

BRIEF SUMMARY OF THE INVENTION

In an exemplary embodiment, the convertible reusable diaper is put together in a three-part construction, comprised of an outer cover portion, a liner portion, and a detachable absorption portion. The impermeable outer cover portion laminated with either a soft pile or a waterproof breathable material may be operably configured to be positioned on a wearer's body and be releasably affixed thereto, including a frontal region, a crotch region, and a posterior region. The outer cover portion may generally include frontal and posterior barrier panels attached at the frontal and posterior regions of the outer cover portion to form interior pockets. The interior pockets allow usage of most disposable and reusable insert products produced by a wide range of vendors. A plurality of fastenable tabs attached to hole-openings at the barrier panels of the outer cover portion affixes the liner portion or the detachable absorption portion in place. The hole-openings allow the passage of the fastenable tabs through the barrier panels so that the fastenable tabs can be affixed either on the outside or the inside of the interior pockets. The liner portion includes a plurality of fastener members cooperatively inter-engaged with the corresponding fastener members located at the fastenable tabs to allow the liner portion to be removably affixed to the outer cover portion. The liner portion is configured to wick moisture from a wearer's body, and fabricated at least in part from liquid-permeable materials that have a short dry time. Other options for the liner portion include natural materials such as cotton, hemp, bamboo, etc. for wearers with exceptionally sensitive skin or for environmentally minded purchasers. The liner portion may be elasticized in any suitable manner to provide a contoured fit around wear's body for preventing leakage. The detachable absorption portion, comprised of at least one insert pad, may be laid onto the outer cover portion or be releasably affixed to the outer cover portion by fastening into the fastenable tabs located at the barrier panels of the outer cover portion. The insert pads come in two size options: long and regular. The regular insert pads have a plurality of fastener members located at one end, which are fastening into the fastenable tabs located at either the frontal barrier panel or the posterior barrier panel. The long insert pads are designed to allow for quicker dry time. In the open configuration, the long insert pad is about one half the thickness of the regular insert pad but double the length. In the closed configuration, the long insert pad is about the same size and shape as the regular insert pad. The fastener members on the long insert pad are located at just below the midpoint of the lengthwise sides of the long insert pads. These fastener members affix to the fastenable tabs on either the frontal barrier panel or the posterior barrier panel. Numerous options for affixing the detachable absorption portion and the liner portion allow easy conversion of the diaper from one design to another. The convertible reusable diaper can serve as a waterproof diaper cover and transform into a pocket diaper and an all-in-two diaper via releasably reaffixing the detachable absorption portion and the liner portion.

In another exemplary embodiment, the convertible reusable diaper may generally include an outer cover portion and a liner portion in accordance with the previous paragraph. The reusable and disposable insert products produced by a wide range of vendors can be inserted between the permeable liner portion and the impermeable outer cover portion. The end corners of the inserts may be fitted into the interior pockets and held firmly in the crotch area by wearer's legs.

In another exemplary embodiment, the convertible reusable diaper may generally include an outer cover portion and a detachable absorption portion in accordance with the previous paragraph.

In another exemplary embodiment, the convertible reusable diaper may generally include an outer cover portion in accordance with the previous paragraph.

Further aspects and features of the present invention will be explained in details in the detailed description section of the document. It should be understood that the detailed description and specific examples indicating exemplary embodiment of the present invention are intended for purposes of illustration only and are not intended to limit the scope of the present invention.

BRIEF DESCRIPTION OF THE SEVERAL VIEWS OF THE DRAWINGS

The drawings described herein are for illustration purpose only and are not intended to limit the scope of the present disclosure in any way.

DETAILED DESCRIPTION OF THE INVENTION

While this inventions is susceptible of embodiment in many different forms, there is shown in the drawings, and described in detail herein, one embodiment, with the understanding that the present disclosure is to be considered an exemplification of the principles of the invention and is not intended to limit the invention to the embodiment illustrated.

The following description and drawings are illustrative and are not to be construed as limiting. Numerous specific details are described to provide a thorough understanding of the disclosure. However, in certain instances, well-known or conventional details are not described in order to avoid obscuring the descriptions. References to one or an embodiment in the present disclosure can be, but not necessarily are, references to the same embodiment; and, such references mean at least one of the embodiments.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way.

Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the disclosure or of any exemplified term. Likewise, the disclosure is not limited to various embodiments given in this specification.

Unless otherwise defined, all technical and scientific terms used herein have the same meaning as commonly understood by one of ordinary skill in the art to which this disclosure pertains. In the case of conflict, the present document, including definitions will control.

According to various aspects, exemplary embodiments are provided of convertible reusable diapers. In one exemplary embodiment, a convertible reusable diaper may comprise an outer cover portion. The outer cover portion may generally include a frontal region, a crotch region, a posterior region, a frontal barrier panel, and a posterior barrier panel. Both the frontal and the posterior barrier panels are attached to the inner surfaces of the frontal and the posterior regions to form a frontal pocket and a posterior pocket, respectively. At least one liquid-absorbent reusable or disposal insert pad may be removably disposed within the outer cover portion with both ends placed in the interior pockets.

In another exemplary embodiment, the convertible reusable diaper is put together in a three-part construction, comprised of an outer cover portion, a liner portion, and a detachable absorption portion. The impermeable outer cover portion laminated with either a soft pile or a waterproof breathable material may be operably configured to be positioned on a wearer's body and be releasably affixed thereto, including a frontal region, a crotch region, and a posterior region. The outer cover portion may generally include frontal and posterior barrier panels attached at the frontal and posterior regions of the outer cover portion to form interior pockets. The interior pockets allow usage of most disposable and reusable insert products produced by a wide range of vendors. A plurality of fastenable tabs attached to hole-openings at the barrier panels of the outer cover portion affixes the liner portion or the detachable absorption portion in place. The hole-openings allow the passage of the fastenable tabs through the barrier panels so that the fastenable tabs can be affixed either on the outside or the inside of the interior pockets. The liner portion includes a plurality of fastener members cooperatively inter-engaged with the corresponding fastener members located at the fastenable tabs to allow the liner portion to be removably affixed to the outer cover portion. The liner portion is configured to wick moisture from a wearer's body, and fabricated at least in part from liquid-permeable materials that have a short dry time. Other options for the liner portion include natural materials such as cotton, hemp, bamboo, etc. for wearers with exceptionally sensitive skin or for environmentally minded purchasers. The liner portion may be elasticized in any suitable manner to provide a contoured fit around wear's body for preventing leakage. The detachable absorption portion, comprised of at least one insert pad, may be laid onto the outer cover portion or be releasably affixed to the outer cover portion by fastening into the fastenable tabs located at the barrier panels of the outer cover portion. The insert pads come in two size options: long and regular. The regular insert pads have a plurality of fastener members located at one end, which are fastening into the fastenable tabs located at either the frontal barrier panel or the posterior barrier panel. The long insert pads are designed to allow for quicker dry time. In the open configuration, the long insert pad is about one half the thickness of the regular insert pad but double the length. In the closed configuration, the long insert pad is about the same size and shape as the regular insert pad. The fastener members on the long insert pad are located at just below the midpoint of the lengthwise sides of the long insert pads. These fastener members affix to the fastenable tabs on either the frontal barrier panel or the posterior barrier panel. Numerous options for affixing the detachable absorption portion and the liner portion allow easy conversion of the diaper from one design to another. The convertible reusable diaper can serve as a waterproof diaper cover and transform into a pocket diaper and an all-in-two diaper via releasably reaffixing the detachable absorption portion and the liner portion.

In another exemplary embodiment, a convertible reusable diaper comprises an outer cover portion and a detachable absorption portion. The outer cover portion may generally include a frontal region, a crotch region, a posterior region, and one or more first fastener members. The outer cover portion may further include a frontal barrier panel and a posterior barrier panel. The frontal barrier panel is attached to the inner surface of the frontal region of the outer cover portion to form a frontal pocket, and the posterior barrier panel is attached to the inner surface of the posterior region of the outer cover portion to form a posterior pocket. The first fastener members can be attached to either the inner surface of the outer cover portion, or the frontal and/or posterior barrier panels when the frontal and posterior barrier panels are included in the outer cover portion. The detachable absorption portion includes one or more second fastener members. One of the second fastener members is cooperatively inter-engaged with one of the first fastener members to allow the detachable absorption portion to be removably affixed to the outer cover portion. The convertible reusable diaper may further include one or more fastener tabs. In one example, one of the first fastener members is attached to one of the fastener tabs which can be attached to either the inner surface of the outer cover portion or the frontal and/or posterior barrier panels when the frontal and posterior barrier panels are included in the outer cover portion. In another example, one of the second fastener members is attached to one of the fastener tabs which can be attached to the detachable absorption portion. The frontal and posterior barrier panels may include one or more hole-openings which allow passage of the fastenable tabs. The detachable absorption portion is configured to be saturated with a diaper wearer's bodily discharges, and fabricated, at least in part, from a liquid-absorbent material. The detachable absorption portion may further include an outer layer which is configured to wick moisture from a diaper wearer's body, and fabricated at least in part from a liquid-permeable material.

In another exemplary embodiment, a convertible reusable diaper comprises an outer cover portion and an liner portion. The outer cover portion may generally include a frontal region, a crotch region, a posterior region, and one or more first fastener members. The outer cover portion may further include a frontal barrier panel and a posterior barrier panel. The frontal barrier panel is attached to the inner surface of the frontal region of the outer cover portion to form a frontal pocket, and the posterior barrier panel is attached to the inner surface of the posterior region of the outer cover portion to form a posterior pocket. The first fastener members can be attached to either the inner surface of the outer cover portion, or the frontal and/or posterior barrier panels when the frontal and posterior barrier panels are included in the outer cover portion. The liner portion includes one or more second fastener members. One of the second fastener members is cooperatively inter-engaged with one of the first fastener members to allow the liner portion to be removably affixed to the outer cover portion. The convertible reusable diaper may further include one or more fastener tabs. In one example, one of the first fastener members is attached to one of the fastener tabs which can be attached to either the inner surface of the outer cover portion or the frontal and/or posterior barrier panels when the frontal and posterior barrier panels are included in the outer cover portion. In another example, one of the second fastener members is attached to one of the fastener tabs which can be attached to the liner portion. The frontal and posterior barrier panels may include one or more hole-openings which allow passages of the fastenable tabs. The liner portion is fabricated, at least in part, from at least one of: a liquid-permeable material configured to wick moisture from a diaper wearer's body, and a natural material configured to reduce irritation of skin of a diaper wearer's body. The liner portion may be elasticized in any suitable manner to provide a contoured fit around a wearer's body for preventing leakage. The convertible reusable diaper may further include at least one removable absorbent pad which is fabricated from materials that are reusable, washable, disposable, and/or biodegradable. The removable absorbent pad may be positioned between the outer cover portion and the liner portion, or deposed within the liner portion. There may be provided a plurality of replacement liners in the liner portion or the removable absorbent pads. In such embodiments, an existing liner or the removable absorbent pad may be removed from the outer cover portion after the removable absorbent pad has become saturated. One of the replacement liners and the removable absorbent pads can be positioned within the outer cover portion after the diaper has been washed or laundered.

In some exemplary embodiments, the outer cover portion, the liner portion, and the detachable absorption portion are configured to be reusable, and fabricated from washable materials. The outer cover portion may further comprise an outer shell which is preferably fabricated from a breathable water proof or water resistant material such as polyester, fleece, wool, and thermoplastic polyurethane laminated material. The liner portion may be fabricated from either natural materials, such as linen, cotton, jute, hemp, bamboo, kenaf, sisal, combinations thereof, etc., or liquid-permeable materials, such as polar fleece, fleece, micro fleece, suede cloth, combinations thereof, etc. The frontal and posterior barrier panels may be fabricated from the same material as the one used by either the outer shell or the liner portion. The detachable absorption portion may be fabricated from a liquid absorbent material, such as linen, hemp, cotton, microfiber, bamboo, polyester or any artificial and synthetic fibre fabric. The fastener members including the first and second fastener members may be selected from a group comprising of adhesives, buttons, clasps, hook and loop closures, magnets, elastic straps, adjustable straps, combinations thereof, etc.

In some exemplary embodiments, the outer cover portion may generally include a frontal region, a crotch region and a posterior region. The posterior region includes snap members located at top corner areas, and the frontal region includes members for being releasably affixed to the posterior region via cooperatively engaging into the corresponding snap members in the posterior region to position the convertible diaper on a diaper wearer's body and allowing adjustable waist size of the convertible reusable diaper. Still further embodiments may include a wide range of other suitable fastening systems besides snaps, such as adhesives, buttons, clasps, hook and loop closures, magnets, elastic straps, adjustable straps, combinations thereof, etc.

In some exemplary embodiments, the outer cover portion may generally include a frontal region, a crotch region and a posterior region. The frontal region includes a plurality of snap members cooperatively inter-engagable to allow adjustable size options on the convertible reusable diaper. In one example, at least a two-by-three array of snap members along the frontal region that allows selective adjustment to a functional rise of the convertible reusable diaper. The array includes at least of first row of at least two spaced-apart snap members vertically spaced from and aligned with corresponding snap members in at least two other rows of the array. Still further embodiments may include a wide range of other suitable fastening systems besides snaps, such as adhesives, buttons, clasps, hook and loop closures, magnets, elastic straps, adjustable straps, combinations thereof, etc.

Figure 1:
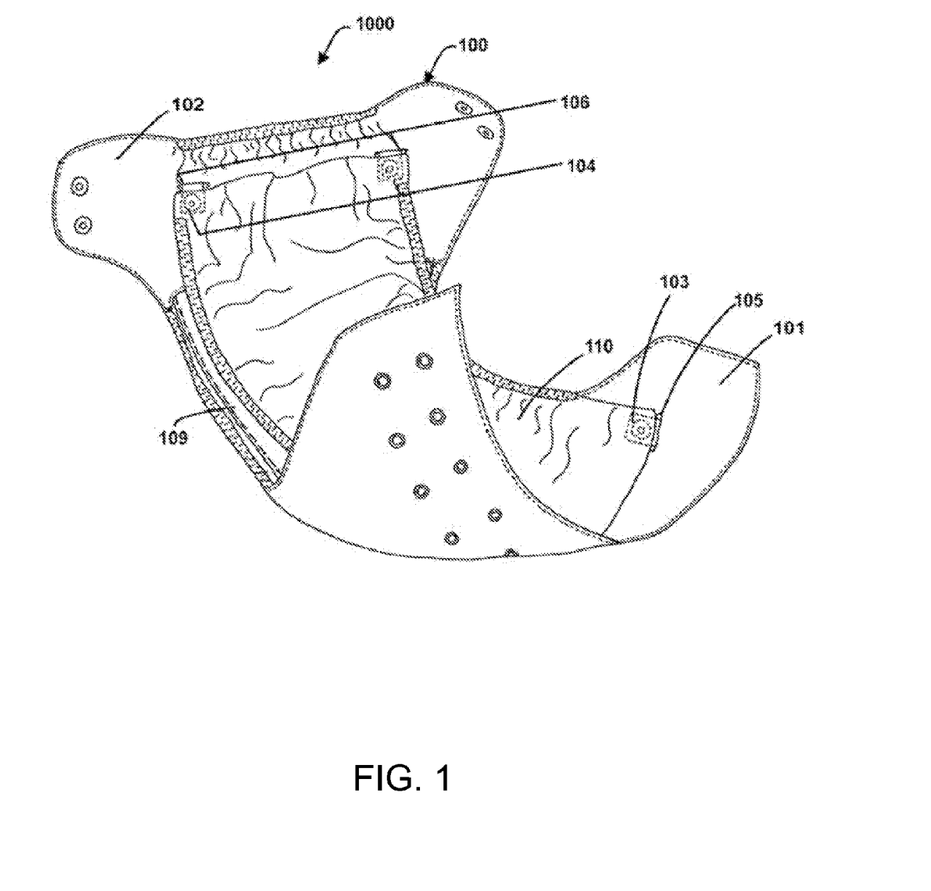
FIG. 1 is a perspective view of the outer cover portion of a convertible reusable diaper with the liner portion and a removable absorbent pad installed, according to an embodiment of the invention.
Figure 2:
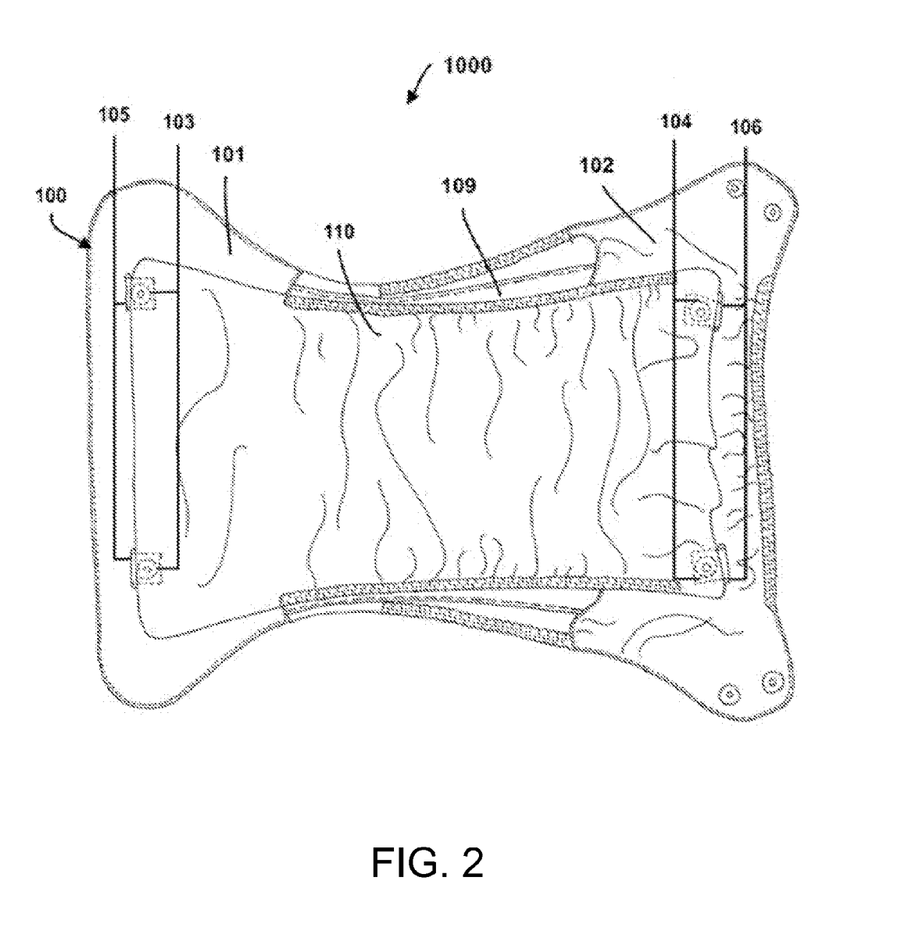
FIG. 2 is a top plan view of the inside of the outer cover portion of a convertible reusable diaper with the liner portion and a removable absorbent pad installed, according to an embodiment of the invention.

FIGS. 1-10 illustrate convertible reusable diaper constructions, in accordance with the principles of the present invention. Referring now to FIG. 1-2, a convertible reusable diaper 1000, in embodiments of the invention, includes an outer cover portion 100, and a liner portion 110. The outer cover portion 100 includes frontal and posterior barrier panels 101 and 102 which are attached to the inner surface of the front and rear top areas of the outer cover portion 100 respectively. The liner portion 110 is releasably affixed to the outer cover portion 100 at four points via fastening into the fastenable tabs 103/104 located at the frontal and posterior barrier panels 101 and 102, covering at least one removable absorbent pad 109 which is disposed within the outer cover portion 100 with two opposite edges placed and retained inside of the frontal and posterior barrier panels 101 and 102. The hole-openings 105/106 on the frontal and posterior barrier panels 101 and 102 allow the passage of the fastenable tabs 103/104 through the frontal and posterior barrier panels 101 and 102 so that the fastenable tabs 103/104 can be affixed either on the outside or the inside of the frontal and posterior barrier panels 101 and 102.

Figure 3:
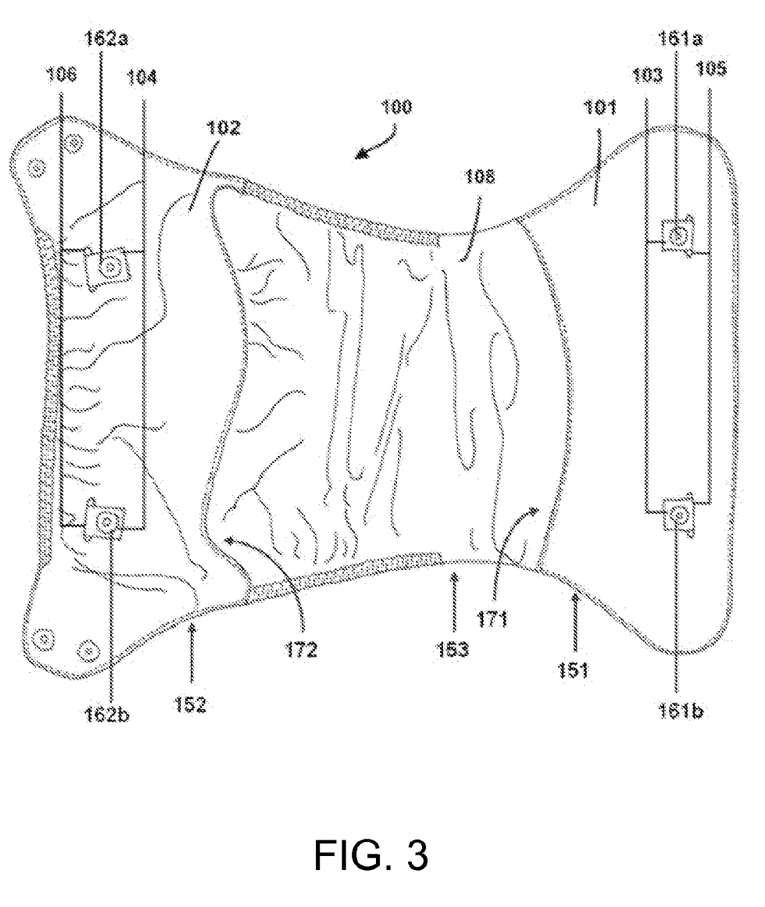
FIG. 3 is a top plan view of the inside of the outer cover portion of a convertible reusable diaper with the fastenable tabs placed on top of the frontal and the posterior barrier panels, according to an embodiment of the invention.
Figure 4:
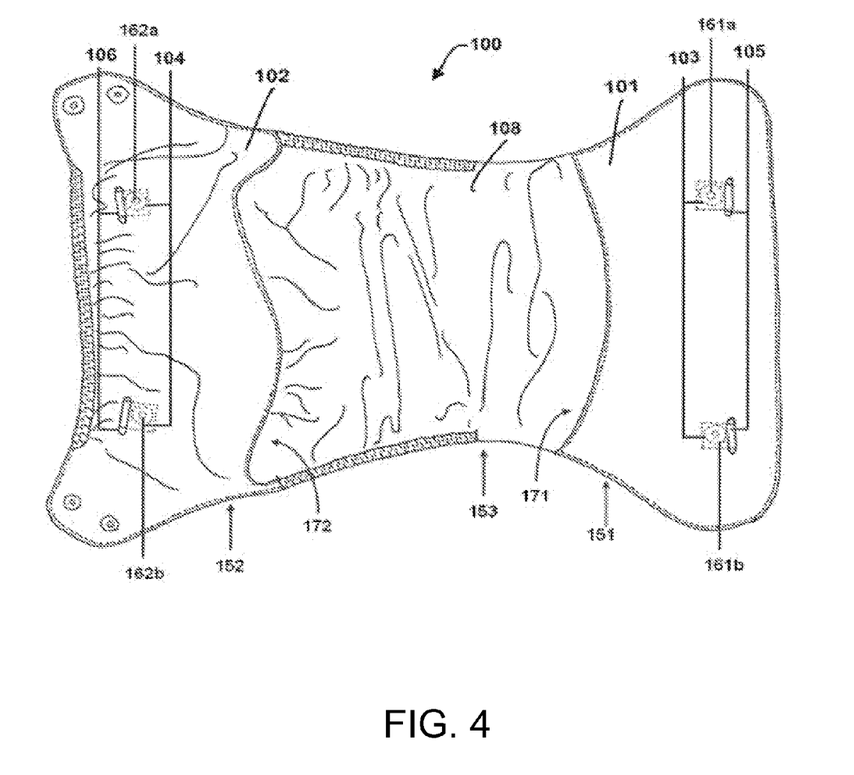
FIG. 4 is a top plan view of the inside of the outer cover portion of a convertible reusable diaper with the fastenable tabs placed underneath of the frontal and the posterior barrier panels, according to an embodiment of the invention.

As shown in FIG. 3, an outer cover portion 100 includes an outer cover shell 108, which is preferably fabricated from a breathable water proof or water resistant material. The frontal and posterior barrier panels 101 and 102 are preferably fabricated from natural materials (such as linen, cotton, jute, hemp, bamboo, kenaf, sisal, etc.), which are configured to minimize irritation of skin of a diaper wearer's body. The frontal and posterior barrier panels 101 and 102 may also be fabricated from liquid-permeable materials (such as polar fleece, fleece, micor fleece, suede cloth, etc.), which have a short dry time and are configured to wick moisture from a diaper wearer's body. Moreover, the frontal and posterior barrier panels 101 and 102 can be fabricated from a breathable water proof or water resistant material for preventing leakage. The frontal barrier panel 101 is attached to the inner surface of the frontal region 151 to form a frontal pocket 171; the posterior barrier panel 102 is attached to the inner surface of the posterior 152 to form a posterior pocket 172. At least one reusable or disposable absorbent pad may be disposed within the outer cover portion 100 with two opposite edges placed and retained inside of the frontal and posterior pockets 171 and 172. A plurality of fastenable tabs 103/104 are attached to the hole-openings 105/106 located on the frontal and posterior barrier panels 101 and 102. The hole-openings 105/106 allow the passage of the fastenable tabs 103/104 through the frontal and posterior panels 101 and 102 so that the fastenable tabs can be placed either on the outside or the inside of the frontal and posterior pockets 171 and 172. The outer cover portion further comprises a plurality of first fastener members 161a, 161b, 162a, 162b which are attached to the corresponding fastener tabs 103/104. As shown in FIG. 4, the fastenable tabs 103/104 can be placed inside of the frontal and posterior pockets 171 and 172 to prevent the fastenable tabs from being exposed to a diaper wearer's skin when the liner portion or the detachable absorption portion is not applixed with the outer cover 100. Therefore, the outer cover 100 can be used as a reusable diaper shell.

Figure 5:
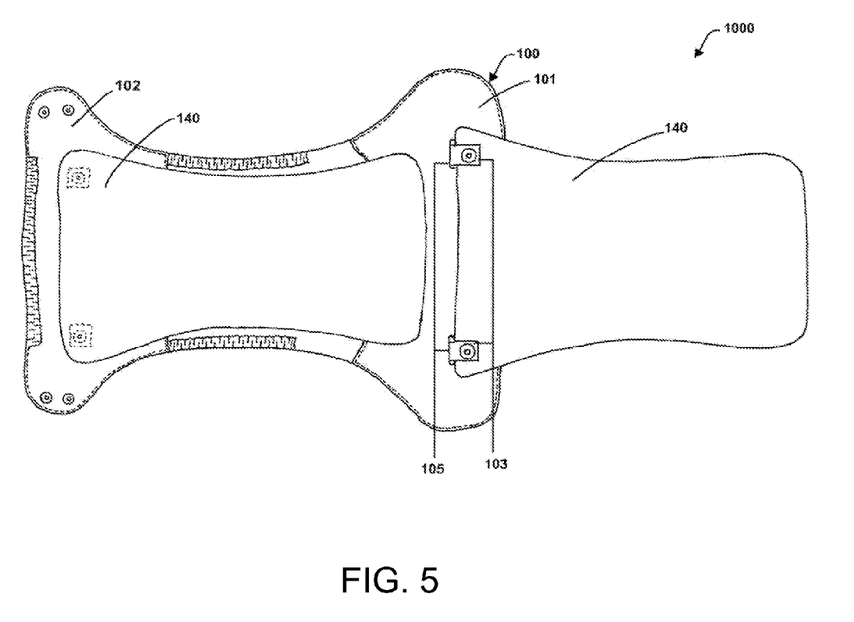
FIG. 5 is top plan view of the inside of the outer cover portion of a convertible reusable diaper with two regular insert pads (shown in FIG. 8) installed on the frontal and the posterior barrier panels of the outer cover portion, according to an embodiment of the invention.

As an embodiment shown in FIG. 5, a convertible reusable diaper 1000 may include at least one regular pad of the detachable absorption portion 140. The regular pad of the detachable absorption portion 140 has one edge releasably affixed to either the frontal or posterior barrier panels 101 or 102 of the outer cover portion 100. The opposite edge and two sides of the regular pad of the detachable absorption portion 140 are not fastened to the frontal and posterior barrier panels 101 and 102 or the outer cover portion 100. As shown in FIG. 5, one regular pad of the detachable absorption portion 140 has one edge releasably affixed to the outer cover portion by fastening into the fastenable tabs 103 passed through the hole-openings 105 located at the frontal barrier panel 101. Using the same method, another regular pad of the detachable absorption portion 140 may be releasably affixed to the posterior barrier panel 102. Therefore, one regular pad of the detachable absorption portion 140 is stacked on top of another to allow customized absorbency.

Figure 6:
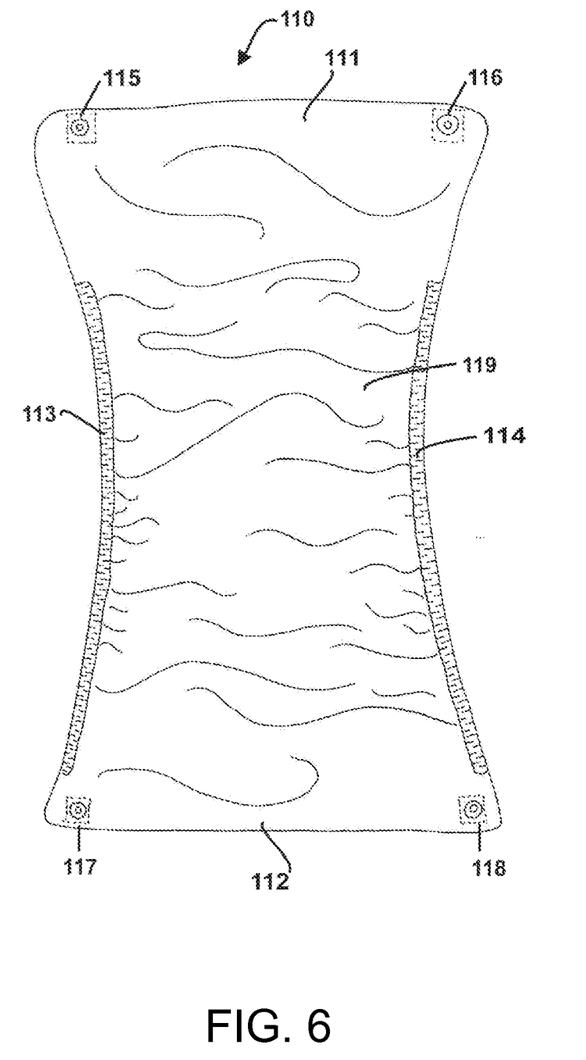
FIG. 6 is a top plan view of the liner portion of a convertible reusable diaper, according to an embodiment of the invention.

As shown in FIG. 6, a liner portion 110 may provide a layer of fabric, liner 119, between a diaper wearer's body and the liquid-absorbent insert pad (s). The liner may be fabricated from a natural material (such as linen, cotton, jute, hemp, bamboo, kenaf, sisal, etc.) or a liquid-permeable material (such as polar fleece, fleece, micor fleece, suede cloth, etc.). The liner portion may generally include a frontal edge 111, a posterior edge 112, and elastic disposed adjacent side edges 113 and 114. A plurality of second fastener members 115, 116, 117, 118 are attached to four corners of the liner portion 110. The second fastener members 115, 116 located at the frontal edge 111 can be cooperatively inter-engaged with the first fastener members 161a, 161b of the fastenable tabs 103 located at the frontal barrier panel 101. The second fastener members 117, 118 located at the posterior edge 112 can be cooperatively inter-engaged with the first fastener members 162a, 162b of the fastenable tabs 104 located at the posterior barrier panel 102. Alternatively, the liquid-absorbent insert pad (s) can be deposed within the liner portion 110.

Figure 7:
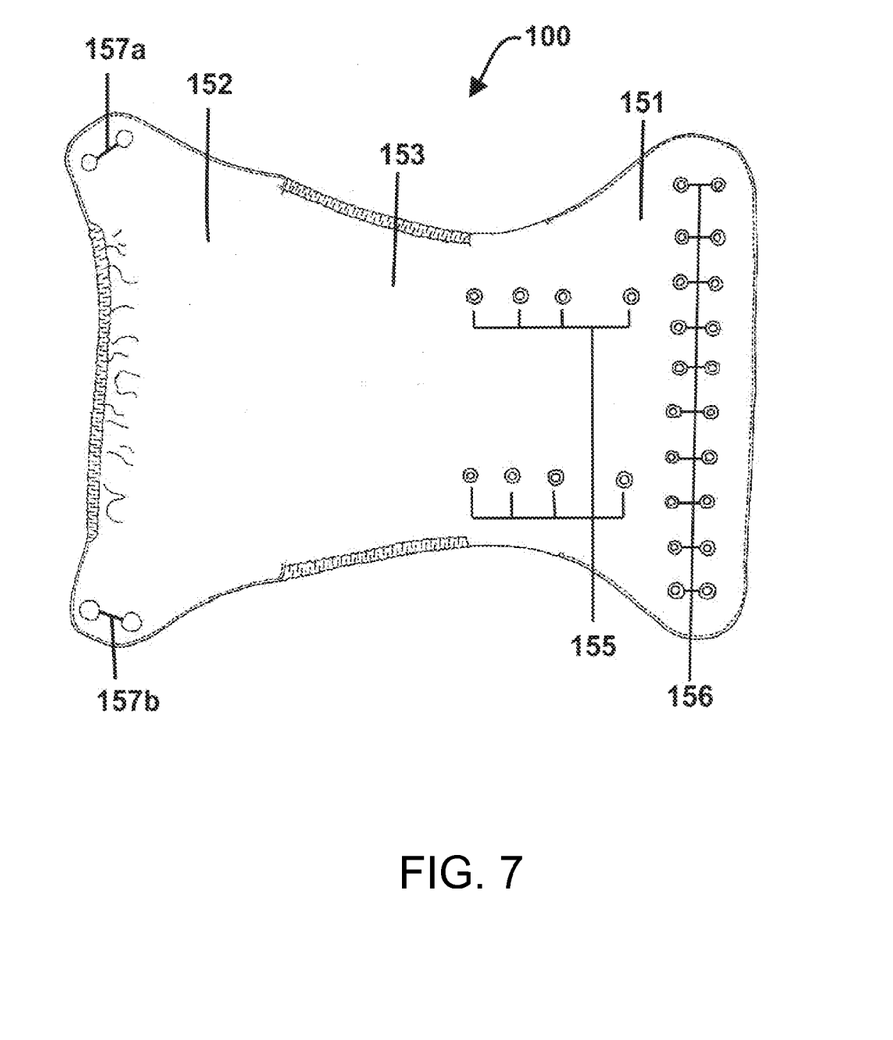
FIG. 7 is a top plan view of the outside of the outer cover portion of a convertible reusable diaper, according to an embodiment of the invention.

FIG. 7 is a top plan view of the outside of the outer cover portion 100. The outer cover portion 100 includes a frontal region 151, a crotch region 153, a posterior region 152. The frontal region 151 includes an array of snap members 155 cooperatively inter-engagable to allow adjustable size options on the convertible reusable diaper 1000. As shown in FIG. 7, at least one two-by-three array of snap members 155 along the frontal region includes at least a first row of at least one space-apart snap members vertically spaced from and aligned with corresponding snap members in at least one other rows of the array. The posterior region 152 includes a plurality of snap members 157a, 157b located at top corner areas of the outer cover portion 100. The frontal region 151 further includes a plurality of snap members 156 for being releasably affixed to the posterior region 152 via engaging into the corresponding snap member 157a, 157b in the corner areas of the posterior region 152 to position the convertible reusable diaper 1000 on a diaper wearer's body and allow adjustable waist size of the convertible reusable diaper 1000. In some preferred embodiments, the frontal region 151 may be releasably attached to the posterior region 152 by using hook-and-loop fasteners. Additional embodiments, however, may alternatively comprise pins, buttons, adhesives, clasps, magnets, combinations thereof, etc.

Figure 8:
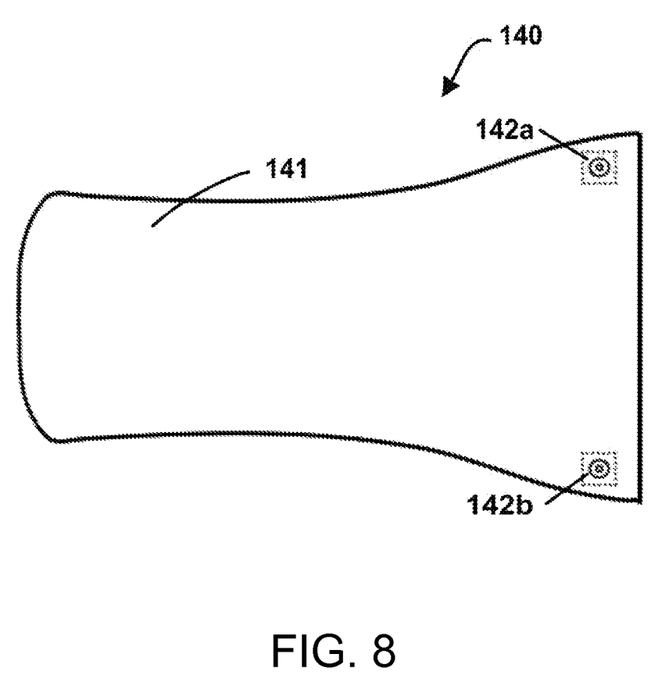
FIG. 8 is a top plan view of a regular insert pad of a convertible reusable diaper, according to an embodiment of the invention.

In FIG. 8, a regular insert pad of the detachable absorption portion 140 has a plurality of second fastener members 142a, 142b located at corners of one edge. The second fastener members 142a, 142b can be cooperatively inter-engaged with either the first fastener members 161a, 161b of the fastenable tabs 103 located at the frontal barrier panel 101 or the first fastener members 162a, 162b of the fastenable tabs 104 located at the posterior barrier panel 102. The regular insert pad of the detachable absorption portion 140 may further include an outer layer 141 which is configured to wick moisture from a diaper wearer's body, and is fabricated at least in part from a liquid-permeable material, such as polar fleece, fleece, micor fleece, suede cloth, etc.

Figure 9:
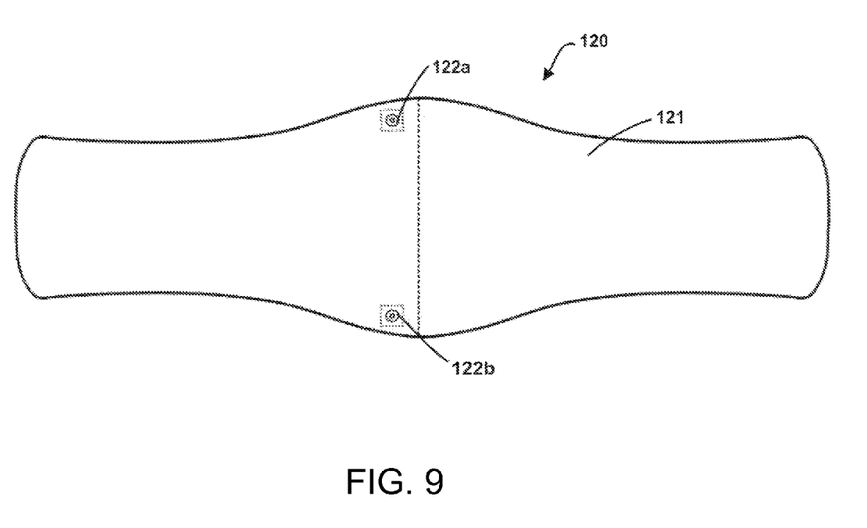
FIG. 9 is a top plan view of a long insert pad of a convertible reusable diaper, according to an embodiment of the invention, shown in an open configuration.

In FIG. 9, a long insert pad of the detachable absorption portion 120 has a plurality of second fastener members 122a, 122b located at just below the midpoint of the lengthwise sides of the long insert pad of the detachable absorption portion 120. In the open configuration shown in FIG. 9, the long insert pad of the detachable absorption portion 120 is about one half the thickness of the regular insert pad of the detachable absorption portion 140 but double the length. In the closed configuration shown in FIG. 10, the long insert pad of the detachable absorption portion 120 is about the same size and shape as the regular insert pad of the detachable absorption portion 140. The second fastener members 122a, 122b can be cooperatively inter-engaged with either the first fastener members 161a, 161b of the fastenable tabs 103 located at the frontal barrier panel 101 or the first fastener members 162a, 162b of the fastenable tabs 104 located at the posterior barrier panel 102. The long insert pad of the detachable absorption portion 120 may further include an outer layer 121 which is configured to wick moisture from a diaper wearer's body, and is fabricated at least in part from a liquid-permeable material, such as polar fleece, fleece, micor fleece, suede cloth, etc.

In some embodiments, one or two regular insert pads of the detachable absorption portion 140 can be removably affixed to the outer cover portion 100. It builds up a convertible reusable diaper 1000 with attached reusable washable liquid-absorbent insert(s).

Figure 10:
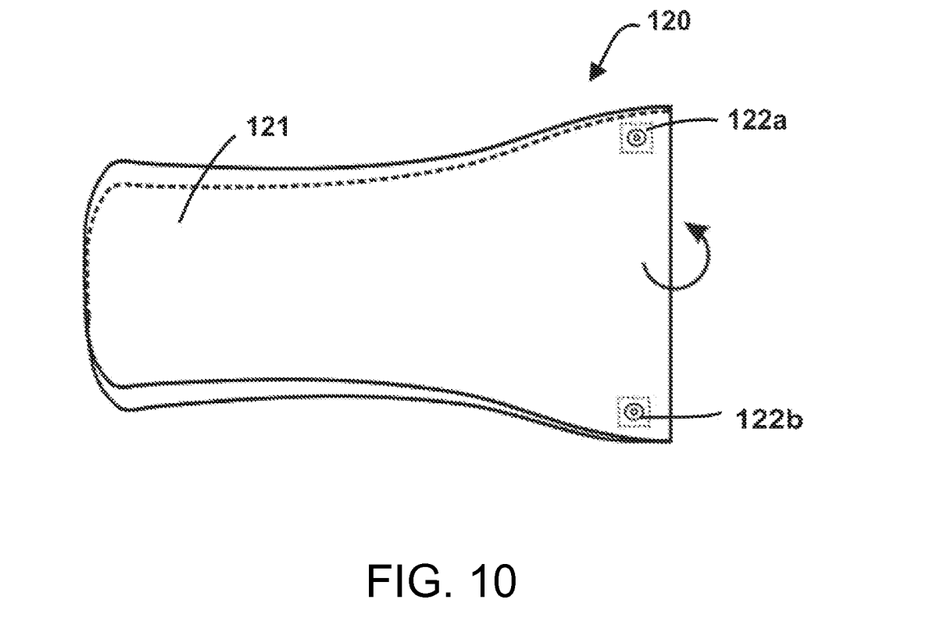
FIG. 10 is a perspective view of a long insert pad of a convertible reusable diaper, according to an embodiment of the invention, shown in a closed configuration.

In some embodiments, one or two long insert pads of the detachable absorption portion 120 can be removably affixed to the outer cover portion 100. It builds up a convertible reusable diaper 1000 with attached reusable washable liquid-absorbent insert(s).

And in other embodiments, a regular insert pad of the detachable absorption portion 140 and a long insert pad of the detachable absorption portion 120 can be mixed together to be removably affixed to the outer cover portion 100 to build another reusable washable liquid-absorbent cloth diaper.

The foregoing description and drawing merely explain and illustrate the invention, and the invention is not limited thereto, except as those skilled in the art who have the present disclosure before them will be able to make modifications and variations therein without departing from the scope of the invention.

The invention claimed is:

1. A convertible reusable diaper comprising:
    an outer cover portion including a frontal region, a crotch region, a posterior region, a frontal barrier panel and a posterior barrier panel;
    a plurality of fastenable tabs affixed to the frontal barrier panel and the posterior barrier panel;
    one or more first fastener members attached to the corresponding fastenable tabs,
    wherein one or more hole-openings are formed on at least one of the frontal barrier panel and the posterior barrier panel allowing the passage of the fastenable tabs;
    a liner portion; and
    one or more second fastener members each of which is attached to the liner portion, wherein at least one of the second fastener members is cooperatively inter-engaged with one of the first fastener members, thereby allowing the liner portion to be removably affixed to the outer cover portion.

2. The convertible reusable diaper of claim 1, wherein the liner portion is configured to be elasticized in a suitable manner to provide a contoured fit around a diaper wearer's body.

3. The convertible reusable diaper of claim 1, wherein the liner portion comprises at least one of polar fleece, fleece, micro fleece and suede cloth.

4. The convertible reusable diaper of claim 1, wherein the liner portion comprises at least one of linen, cotton, jute, hemp, bamboo, kenaf and sisal.

5. The convertible reusable diaper of claim 1, wherein the first and second fastener members are selected from among a group comprising: buttons, snaps, pins, adhesives, clasps, magnets, hooks and loop closures, elastic straps, adjustable straps.

6. The convertible reusable diaper of claim 1, wherein the frontal region of the outer cover portion includes a plurality of snap members cooperatively inter-engagable to thereby allow adjustable size options on the convertible reusable diaper.

7. The convertible reusable diaper of claim 1, wherein the posterior region of the outer cover portion includes snap members located at top corner areas, and wherein the frontal region includes snap members for being releasably affixed to the posterior region via cooperatively engaging into the corresponding snap members in the posterior region, whereupon positioning of the convertible diaper on a diaper wearer's body and allowing adjustable waist size of the convertible reusable diaper.

8. The convertible reusable diaper of claim 1, wherein the outer cover portion further comprises an outer shell fabricated from at least one of: polyester, fleece, wool, and thermoplastic polyurethane laminated material.

9. The convertible reusable diaper of claim 1, wherein the outer cover portion and the liner portion are configured to be reusable, and are fabricated from washable materials.

10. The convertible reusable diaper of claim 1, wherein the liner portion is fabricated, at least in part, from at least one of: a liquid-permeable material configured to wick moisture from a diaper wearer's body, and a natural material configured to reduce irritation of skin of a diaper wearer's body.

11. The convertible reusable diaper of claim 1, wherein at least one removable absorbent pad is positioned between the outer cover portion and the liner portion.

12. The convertible reusable diaper of claim 11, wherein the removable absorbent pad is reusable and washable, and wherein the removable absorbent pad is fabricated from liquid-absorbent materials.

13. The convertible reusable diaper of claim 11, wherein the removable absorbent pad is fabricated from materials that are disposable and/or biodegradable.

14. A convertible reusable diaper comprising:
an outer cover portion including a frontal region, a crotch region, a posterior region, a frontal barrier panel and a posterior barrier panel, wherein the frontal barrier panel is attached to an inner surface of the frontal region to form a frontal pocket, and wherein the posterior barrier panel is attached to an inner surface of the posterior region to form a posterior pocket;
a plurality of fastenable tabs placed inside the frontal pocket and the posterior pocket;
one or more first fastener members attached to the corresponding fastenable tabs,
wherein one or more hole-openings are formed on at least one of the frontal barrier panel and the posterior barrier panel allowing the passage of the fastenable tabs;
a detachable absorption portion; and
a plurality of second fastener members attached to the detachable absorption portion, wherein one of the second fastener members is cooperatively inter-engaged with one of the first fastener members, thereby allowing the detachable absorption portion to be removably affixed to the outer cover portion.

15. The convertible reusable diaper of claim 14, wherein the detachable absorption portion includes an outer layer configured to wick moisture from a diaper wearer's body, and wherein the detachable absorption portion is fabricated at least in part from a liquid-permeable material.

16. The convertible reusable diaper of claim 15, wherein the liquid-permeable material includes one or more of: polar fleece, fleece, micro fleece, and suede cloth.

17. The convertible reusable diaper of claim 14, wherein the first and second fastener members are selected from a group comprising: buttons, snaps, pins, adhesives, clasps, magnets, hooks and loop closures, elastic straps, adjustable straps.

18. The convertible reusable diaper of claim 14, wherein the frontal region includes a plurality of snap members cooperatively inter-engagable, thereby allowing adjustable size options on the convertible reusable diaper.

19. The convertible reusable diaper of claim 14, wherein the posterior region includes snap members located at top corner areas, and wherein the frontal region includes snap members for being releasably affixed to the posterior region via engaging into the corresponding snap members in the posterior region, whereupon positioning of the convertible reusable diaper on a diaper wearer's body and allowing adjustable waist size of the convertible reusable diaper.

20. The convertible reusable diaper of claim 14, wherein the outer the cover portion further comprises an outer shell fabricated from at least one of: polyester, fleece, wool, and thermoplastic polyurethane laminated material.

* * * * *